(12) United States Patent
Chen et al.

(10) Patent No.: US 11,001,800 B2
(45) Date of Patent: May 11, 2021

(54) MICROALGAE CULTURING METHOD BY USING PAPER BASED CULTURE APPARATUS

(71) Applicant: TIANJIN UNIVERSITY, Tianjin (CN)

(72) Inventors: Guanyi Chen, Tianjin (CN); Daohong Zhang, Tianjin (CN); Beibei Yan, Tianjin (CN); Zhan Hu, Tianjin (CN); Yun Qi, Tianjin (CN)

(73) Assignee: TIANJIN UNIVERSITY, Tianjin (CN)

( * ) Notice: Subject to any disclaimer, the term of this patent is extended or adjusted under 35 U.S.C. 154(b) by 20 days.

(21) Appl. No.: 16/598,887

(22) Filed: Oct. 10, 2019

(65) Prior Publication Data

US 2020/0040299 A1     Feb. 6, 2020

Related U.S. Application Data

(63) Continuation of application No. PCT/CN2017/085869, filed on May 25, 2017.

(30) Foreign Application Priority Data

Apr. 17, 2017 (CN) .......................... 201710249837.3

(51) Int. Cl.
    *C12N 1/12*          (2006.01)
    *C12M 1/12*          (2006.01)
    *C12M 1/00*          (2006.01)
    *C12N 15/10*         (2006.01)

(52) U.S. Cl.
CPC ............... *C12N 1/12* (2013.01); *C12M 23/04* (2013.01); *C12M 23/20* (2013.01); *C12N 15/1017* (2013.01)

(58) Field of Classification Search
CPC .......... C12N 1/12; C12M 23/04; C12M 23/20
See application file for complete search history.

(56) References Cited

FOREIGN PATENT DOCUMENTS

| CN | 101978272 A | 2/2011 |
|---|---|---|
| CN | 102373156 A | 3/2012 |
| CN | 103834567 A | 6/2014 |
| CN | 104677896 A | 6/2015 |

OTHER PUBLICATIONS

Ng, K. et al. Paper-based cell culture platform and its emerging biomedical applications. (Feb. 2017). 20(1), 32-44. (Year: 2017).*
International search report of PCT/CN2017/085869.
Written opinion of PCT/CN2017/085869.

* cited by examiner

*Primary Examiner* — Nghi V Nguyen
*Assistant Examiner* — Kevin Greenwood
(74) *Attorney, Agent, or Firm* — Dragon Sun Law Firm, PC; Jinggao Li, Esq.

(57) ABSTRACT

A microalgae culturing method by using a paper-based culture apparatus, includes: 1) designing the shape of a culture apparatus as a rectangle with circles distributed in its middle; 2) spraying and printing wax on a piece of filter paper; 3) heating such that the wax penetrates through the filter paper to obtain a paper culture apparatus, where a surface of the filter paper on which the wax is sprayed and printed is called a surface A while the other surface thereof is called a surface B; and 4) dropping a first agar aqueous solution onto the circles on the surface B of the paper culture apparatus obtained in the step 3), and dropping a second agar aqueous solution added with microalgae onto the surface A of the paper culture apparatus obtained in the step 3).

4 Claims, 2 Drawing Sheets

MICROALGAE CULTURING METHOD BY USING PAPER BASED CULTURE APPARATUS

CROSS-REFERENCE TO RELATED APPLICATIONS

This application is a bypass continuation application of PCT Application No. PCT/CN2017/085869. This Application claims priority from PCT Application No. PCT/CN2017/085869, filed May 25, 2017, CN Application No. 201710249837.3 filed Apr. 17, 2017, the contents of which are incorporated herein in the entirety by reference.

Some references, which may include patents, patent applications, and various publications, are cited and discussed in the description of the present disclosure. The citation and/or discussion of such references is provided merely to clarify the description of the present disclosure and is not an admission that any such reference is "prior art" to the present disclosure described herein. All references cited and discussed in this specification are incorporated herein by reference in their entireties and to the same extent as if each reference was individually incorporated by reference.

TECHNICAL FIELD

The present invention belongs to the technical field of microalgae culturing methods, and particularly relates to a microalgae culturing method by using a paper-based culture apparatus.

BACKGROUND OF THE PRESENT INVENTION

The research and development of alternative energy sources for fossil fuel is an important field of scientific researches worldwide. As an importance one of new fuels, the biodiesel has the advantages such as non-toxic, excellent lubricity, safety and combustion performances, and is biodegradable and environmentally-friendly. Therefore, the researches on the utilization of biodiesel and biomass energy have been vigorously promoted in various countries in the world.

Microalgae is regarded as a unique raw material that can completely replace the fossil fuel. The preparation of biodiesel from microalgae includes three important steps, i.e., selecting microalgae, culturing microalgae, and harvesting and processing microalgae. Although microalgae have enormous potential, the use of microalgae as a biological energy source is still restricted by the scale and cost.

The selection of microalgae is generally performed by a solid culture medium, but the selection of culture conditions and oil accumulation conditions are usually performed in a liquid culture medium. Lots of experiments for selecting culture conditions will consume a certain amount of resources. Common microalgae culturing methods include open large-pool culturing method, enclosed photobioreactor culturing method, heterotrophic culturing method or the like. However, a large space and a large amount of manpower and material resources are required in these culturing methods. Meanwhile, since microalgae individuals are tiny and the concentration of microalgae in the culture solution is very low, it is very difficult for harvesting. The methods for harvesting microalgae include centrifugation, flocculation, foam separation, microfiltration and the like. The cost for harvesting still accounts for 20% to 30% of the cost for cultivation. Since the water body and environment pollution generated during the cultivation and harvesting of microalgae also needs to be further treated, the cost for cultivation is increased.

The immobilized production of microalgae can overcome the disadvantages of low growth density, large volume, difficult harvesting and the like, and thus has a very promising prospect. However, the immobilization technology for microalgae is still not perfect, and there are some disadvantages such as high cost for immobilization materials. Therefore, it is urgent to provide a microalgae culturing method with low cost, less occupation and a small amount of microalgae of performing experiments for selecting culture conditions and oil accumulation conditions; moreover, the cultured microalgae is very high in density and will not be harvested in a subsequent stage; and the method does not pollute the environment.

Therefore, a heretofore unaddressed need exists in the art to address the aforementioned deficiencies and inadequacies.

SUMMARY OF THE PRESENT INVENTION

In order to overcome the deficiencies of the prior art, an objective of the present invention is to provide a microalgae culturing method by using a paper-based culture apparatus, which is environmentally-friendly and can reduce experimental research and production cost.

The technical solutions of the present invention will be described below.

A microalgae culturing method by using a paper-based culture apparatus is provided, including the following steps of:

1) designing a shape of a culture apparatus as a rectangle with circles (1) distributed in its middle;

2) spraying and printing wax on a piece of filter paper according to the design in the step 1) by a wax spray printer, wherein the wax is printed on a part (2) of the rectangle other than the circles;

3) heating such that the wax penetrates through the filter paper to obtain a paper culture apparatus, wherein a surface of the filter paper on which the wax is sprayed and printed is called a surface A, while the other surface thereof is called a surface B;

4) culturing microalgae: dropping a first agar aqueous solution onto the circles on the surface B of the paper culture apparatus obtained in the step 3), and dropping a second agar aqueous solution added with microalgae onto the circles on the surface A of the paper culture apparatus obtained in the step 3), and condensing the agar aqueous solutions on the surface A and surface B; and 5) immersing the surface B of the apparatus obtained in the step 4) into a glass culture dish containing a BG-11 culture solution for culturing;

wherein the first agar aqueous solution is prepared by the following method: weighing 0.8 g to 1.5 g of agar, adding water to 100 mL, mixing uniformly, and heating to dissolve; and the second agar aqueous solution is prepared by the following method: weighing 0.1 g to 0.5 g of agar, adding water to 100 mL, mixing uniformly, and heating to dissolve.

The number of circles on the culture apparatus ranges from 6 to 96, preferably, number of circles is selected from one of the following numbers: 6, 12, 24, 48 or 96.

Preferably, the filter paper is a piece of qualitative filter paper or quantitative filter paper.

The culturing condition in the step (4) is as follows: irradiating at the temperature within the ranges from 20° C. to 35° C. for 4 to 8 days.

The present invention has the following advantages.

1. By culturing microalgae through a paper culture apparatus of the present invention, the operation is simplified, the space required is reduced, and the cost is reduced.
2. By using a small amount of microalgae, the selection of culture conditions and oil accumulation conditions can be carried out.
3. It is convenient for repetitive experiments.
4. The microalgae is cultured in an immobilized manner without harvesting, and the yield per unit area is high.
5. The technology used in the present invention can be applied to raw materials such as marine microalgae and freshwater microalgae, as long as the microalgae is immobilized by agar gels with different densities according to the size of different microalgae.
6. The method is environmental-friendly.

BRIEF DESCRIPTION OF THE DRAWINGS

The accompanying drawings illustrate one or more embodiments of the present invention and, together with the written description, serve to explain the principles of the invention. Wherever possible, the same reference numbers are used throughout the drawings to refer to the same or like elements of an embodiment.

DETAILED DESCRIPTION OF THE PRESENT INVENTION

In order to make the technical solutions and features of the present invention clearer, the present invention will be further described below with reference to the accompanying drawings by specific implementations. The specific embodiments described herein are merely for explaining the present invention rather than limiting the protection scope of the present invention.

In the present invention, the wax spray printer will not be limited. The used wax spray printer is selected from the groups consisting of: Xerox ColorQube 8580, Xerox ColorQube 8700, Xerox ColorQube 8880 or Xerox ColorQube 8900. Xerox ColorQube 8700 is used in various embodiments of the present invention.

The microalgae (*Desmodesmus brasiliensis*) was purchased from the Aquatic Algae Seed Library of the Chinese Academy of Sciences in October 2015.

The term "BG-11" is used herein generically refers to algae culture medium with following components (in 1.0 liter medium):

$NaNO_3$ 1.5 g, $K_2HPO_4$ 0.04 g, $MgSO_4 \cdot 7H_2O$ 0.075 g, $CaCl_2 \cdot 2H_2O$ 0.036 g, citric acid 0.006 g, ferric ammonium citrate 0.006 g, EDTA (disodium salt) 0.001 g, $Na_2CO_3$ 0.02 g, $H_3BO_3$ 2.86 g, $MnCl_2 \cdot 4H_2O$ 1.81 g, $ZnSO_4 \cdot 7H_2O$ 0.222 g, $NaMoO_4 \cdot 2H_2O$ 0.39 g, $CuSO_4 \cdot 5H_2O$ 0.079 g, $Co(NO_3)_2 \cdot 6H_2O$ 49.4 mg.

The term gel" used herein refers to a solid material generated by cooling down an aqueous solution.

*Desmodesmus brasiliensis* is an example of microalgae in the present invention, but the microalgae will not be limited in the present invention. Experiments show that other kinds of microalgae can also be cultured by the apparatus of the present invention.

Embodiment 1

Figure 1:
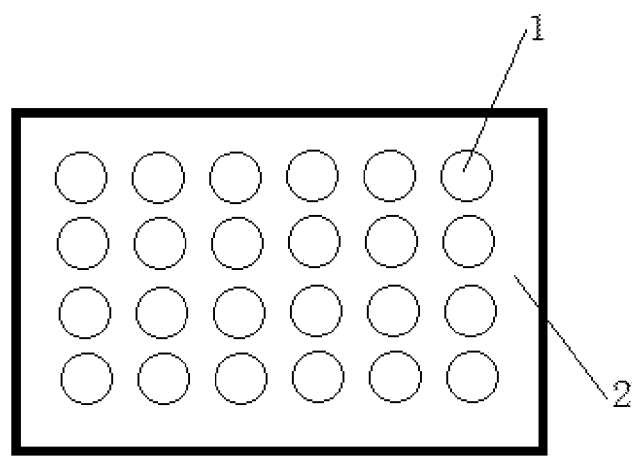
FIG. 1 is a diagram of a culture apparatus with 24 circles.
Figure 2:
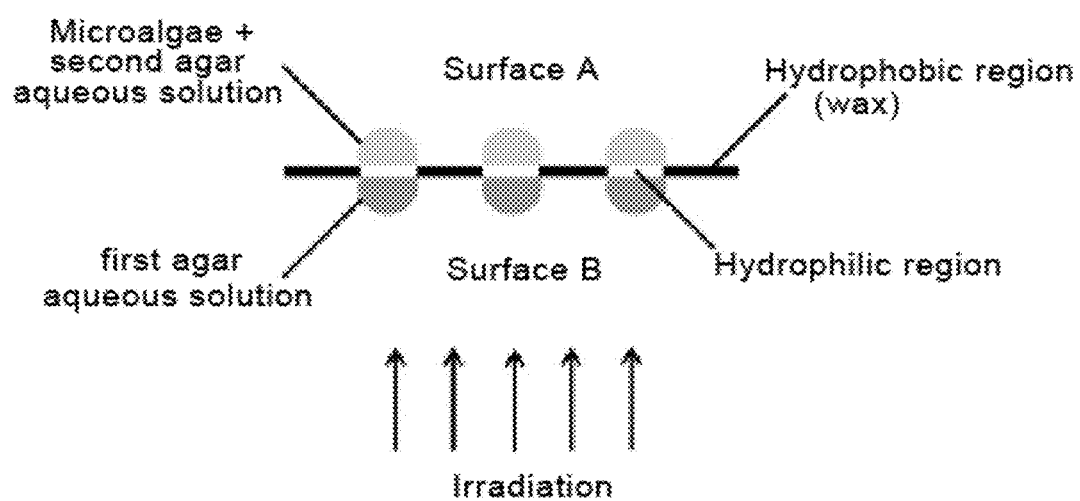
FIG. 2 is a schematic diagram of culturing microalgae by a paper culture apparatus.

A microalgae culturing method by using a paper-based culture apparatus is provided. As shown in FIG. 1 and FIG. 2, the method includes the following steps.

1) The shape of a culture apparatus is designed on a computer, wherein the shape of the culture apparatus is a rectangle with 24 circles 1 distributed in its middle, and the circles each have a diameter of 5.0 mm.

2) Wax is sprayed and printed on a piece of filter paper according to the design in the step 1) by a wax spray printer, wherein the wax is printed on a part 2 of the rectangle other than the circles.

3) The wax-printed filter paper is put in a heating plate and then heated at the temperature of 140° C. for 3 min such that the wax penetrates through the filter paper to form a hydrophobic region and a hydrophilic region is formed at the circles, so that a paper culture apparatus is obtained. A surface of the filter paper on which the wax is sprayed and printed is called a surface A, while the other surface thereof is called a surface B.

4) Culture of the microalgae (*Desmodesmus brasiliensis*): 20 μL of a first agar aqueous solution is dropped onto the circles on the surface B of the paper culture apparatus obtained in the step 3), and 10 μL of a second agar aqueous solution added with microalgae is dropped onto the circles on the surface A of the paper culture apparatus obtained in the step 3); wherein the second agar aqueous solution added with microalgae is obtained by mixing the microalgae solution having the optical density (hereinafter referred to as OD, with maximum light absorption wavelength of 680 nm) of 4.2 cultured in the BG-11 culture solution with the second agar aqueous solution at a volume ratio of 1:4.

Figure 3:
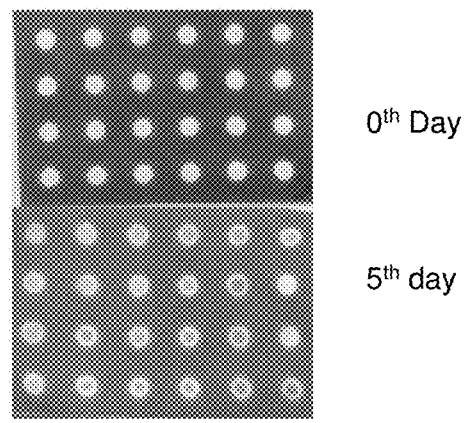
FIG. 3 shows the results of culturing microalgae in the paper culture apparatus on the $0^{th}$ day and the $5^{th}$ day.

5) The surface B of the apparatus obtained in the step 4) is immersed into a 90 mm glass culture dish containing 10 mL of the BG-11 culture solution and then irradiated at the temperature of 25° C. under an irradiation intensity of 2000 lx for 5 days for culturing, and the microalgae is harvested (the paper culture apparatus with 24 circles is taken out and dried), wherein the obtained OD is greater than 8.0, as shown in FIG. 3.

The first agar aqueous solution is prepared by the following method: weighing 1.0 g of agar, adding water to 100 mL, mixing uniformly, and heating to dissolve.

The second agar aqueous solution is prepared by the following method: weighing 3.0 g of agar, adding water to 100 mL, mixing uniformly, and heating to dissolve.

The microalgae is very high in density and adhered onto the agar gel, and the microalgae is harvested without going through centrifugation, flocculation or the like. The method saves cost for harvesting, and prevents the pollution to the water body by any flocculating agent. Meanwhile, since the microalgae only exist in the agar gel, the culture solution can be reused.

Each circle in the culture apparatus is equivalent to a conical flask in the conventional conical flask culture method. Therefore, the paper culture apparatus with 24 circles is equivalent to 24 conical flasks. Consequently, the method of the present invention can greatly save the culture space and material consumption.

Embodiment 2

A microalgae culturing method by using a paper-based culture apparatus is provided. The method includes the following steps.

1) The shape of a culture apparatus is designed on a computer, wherein the shape of the culture apparatus is a rectangle with 6 circles distributed in its middle, and the circles each have a diameter of 7.8 mm.

2) Wax is sprayed and printed on a piece of filter paper according to the design in the step 1) by a wax spray printer, wherein the wax is printed on a part of the rectangle other than the circles.

3) The wax-printed filter paper is put in a heating plate and then heated at the temperature of 120° C. for 5 min such that the wax penetrates through the filter paper to form a hydrophobic region and a hydrophilic region is formed at the circles, so that a paper culture apparatus is obtained. A surface of the filter paper on which the wax is sprayed and printed is called a surface A, while the other surface thereof is called a surface B.

4) Culture of the microalgae (*Desmodesmus brasiliensis*): 15 μL of a first agar aqueous solution is dropped onto the circles on the surface B of the paper culture apparatus obtained in the step 3), and 15 μL of a second agar aqueous solution added with microalgae is dropped onto the circles on the surface A of the paper culture apparatus obtained in the step 3); wherein the second agar aqueous solution added with microalgae is obtained by mixing the microalgae solution (OD of 4.2) cultured in the BG-11 culture solution with the second agar aqueous solution at a volume ratio of 1:4.

5) The surface B of the apparatus obtained in the step 4) is immersed into a 90 mm glass culture dish containing 10 mL of the BG-11 culture solution and then irradiated at the temperature of 20° C. under an irradiation intensity of 2000 lx for 8 days for culture, and the microalgae is harvested (the paper culture apparatus with 6 circles is taken out and dried), wherein the obtained OD is greater than 8.0.

The first agar aqueous solution is prepared by the following method: weighing 0.8 g of agar, adding water to 100 mL, mixing uniformly, and heating to dissolve.

The second agar aqueous solution is prepared by the following method: weighing 0.1 g of agar, adding water to 100 mL, mixing uniformly, and heating to dissolve.

Embodiment 3

A microalgae culturing method by using a paper-based culture apparatus is provided. The method includes the following steps.

1) The shape of a culture apparatus is designed on a computer, wherein the shape of the culture apparatus is a rectangle with 96 circles distributed in its middle, and the circles each have a diameter of 5.0 mm.

2) Wax is sprayed and printed on a piece of filter paper according to the design in the step 1) by a wax spray printer, wherein the wax is printed on a part of the rectangle other than the circles.

3) The wax-printed filter paper is put in a heating plate and then heated at the temperature of 150° C. for 0.5 min such that the wax penetrates through the filter paper to form a hydrophobic region and a hydrophilic region is formed at the circles, so that a paper culture apparatus is obtained. A surface of the filter paper on which the wax is sprayed and printed is called a surface A, while the other surface thereof is called a surface B.

4) Culture of the microalgae (*Desmodesmus brasiliensis*): 15 μL of a first agar aqueous solution is dropped onto the circles on the surface B of the paper culture apparatus obtained in the step 3), and 15 μL of a second agar aqueous solution added with microalgae is dropped onto the circles on the surface A of the paper culture apparatus obtained in the step 3); wherein the second agar aqueous solution added with microalgae is obtained by mixing the microalgae solution (OD of 4.2) cultured in the BG-11 culture solution with the second agar aqueous solution at a volume ratio of 1:4.

5) The surface B of the apparatus obtained in the step 4) is immersed into a 90 mm glass culture dish containing 10 mL of the BG-11 culture solution and then irradiated at the temperature of 35° C. under an irradiation intensity of 2000 lx for 4 days for culture, and the microalgae is harvested (the paper culture apparatus with 96 circles is taken out and dried), where the obtained OD is greater than 8.0.

The first agar aqueous solution is prepared by the following method: weighing 1.5 g of agar, adding water to 100 mL, mixing uniformly, and heating to dissolve.

The second agar aqueous solution is prepared by the following method: weighing 0.5 g of agar, adding water to 100 mL, mixing uniformly, and heating to dissolve.

Embodiment 4

Single-Salt Concentration Test

The steps 1), 2) and 3) in this embodiment are the same as the steps 1), 2) and 3) in Embodiment 1.

4) Culture of the microalgae (*Desmodesmus brasiliensis*): 20 μL of a first agar aqueous solution is dropped onto the circles on the surface B of the paper culture apparatus obtained in the step 3); the microalgae solution cultured in the BG-11 culture solution is centrifuged to remove the culture solution, and the microalgae is suspended in ultrapure water to obtain a microalgae solution having an OD of 4.0; the microalgae solution is mixed with a second agar aqueous solution at a volume ratio of 1:4; 10 μL of the mixed solution is dropped onto the circles on the surface A of the paper culture apparatus obtained in the step 3); and, a salt aqueous solution is dropped onto the coagulated microalgae gel, wherein the volume of the dropped salt aqueous solution is 4 μL.

Salt Solutions:
the concentration of the $K_2HPO_4$ solution is 1.0 g/L;
the concentration of the $NaNO_3$ solution is 37.5 g/L;
the concentration of the $Na_2CO_3$ solution is 0.5 g/L;
the concentration of the $CaCl_2.H_2O$ solution is 0.9 g/L;
the concentration of the $MgSO_4.7H_2O$ solution is 1.875 g/L.

Positive control: the above five salts with the same concentrations as above.

Negative control: water.

5) The surface B of the apparatus obtained in the step 4) is immersed into a 90 mm glass culture dish containing 10 mL of the BG-11 culture solution and then irradiated at the temperature of 25° C. under an irradiation intensity of 2000 lx for 5 days for culture, and the microalgae is harvested (the paper culture apparatus is taken out and dried), where the obtained OD is greater than 8.0.

The first agar aqueous solution is prepared by the following method: weighing 1.0 g of agar, adding water to 100 mL, mixing uniformly, and heating to dissolve.

The second agar aqueous solution is prepared by the following method: weighing 0.3 g of agar, adding water to 100 mL, mixing uniformly, and heating to dissolve.

Figure 4:
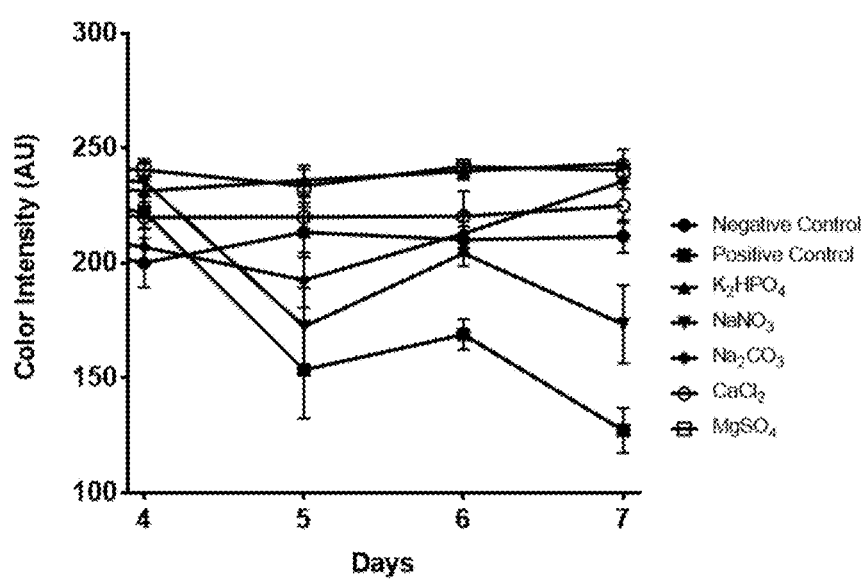
FIG. 4 shows the influence of a single salt on the growth of microalgae.

The results of microalgae culture are shown in FIG. 4. By comparing the three main nutrients (i.e., the P source, the N source and the C source), the microalgae added with $NaNO_3$ grows fastest, so the N source is a necessary nutrient for the growth of the microalgae; the microalgae added with $Na_2CO_3$ grows faster in the early state but grows slowly in the later stage, possibly because the C source is consumed faster and the addition of the single P source does not promote the growth of the microalgae. By comparing the two trace elements Ca and Mg, the growth rate of the microalgae added with $CaCl_2$ is slower than that of the negative control, possibly because excessive single Ca ions inhibit the growth of the microalgae or promote the oil accumulation; and, the growth rate of the microalgae added with $MgSO_4.7H_2O$ is also slower than that of the negative control, possibly the addition of Mg results of the accumulation of chlorophyll and thus inhibits the growth of the microalgae. Since the five salts are added in the positive control, the growth rate is fastest.

Experiments show that the volume ratio of the microalgae to the second agar aqueous solution in various embodiments may also be 1:5, 1:6, 1:7 or the like.

The foregoing description of the exemplary embodiments of the present invention has been presented only for the purposes of illustration and description and is not intended to be exhaustive or to limit the invention to the precise forms disclosed. Many modifications and variations are possible in light of the above teaching.

The embodiments were chosen and described in order to explain the principles of the invention and their practical application so as to activate others skilled in the art to utilize the invention and various embodiments and with various modifications as are suited to the particular use contemplated. Alternative embodiments will become apparent to those skilled in the art to which the present invention pertains without departing from its spirit and scope. Accordingly, the scope of the present invention is defined by the appended claims rather than the foregoing description and the exemplary embodiments described therein.

What is claimed is:

1. A method of preparing a paper-based culture apparatus for culturing microalgae thereon, comprising:
   1) designing a shape of a culture apparatus as a rectangle with circles (1) distributed in its middle;
   2) printing wax on a piece of filter paper according to the design in the step 1) by a wax spray printer, wherein the wax is printed on a part (2) of the rectangle other than the circles;
   3) heating such that the wax penetrates through the filter paper to obtain a paper culture apparatus, wherein a surface of the filter paper on which the wax is sprayed and printed is called a surface A while the other surface thereof is called a surface B;
   4) culturing microalgae: dropping a first agar aqueous solution onto the circles on the surface B of the paper culture apparatus obtained in the step 3), and dropping a second agar aqueous solution added with microalgae onto the circles on the surface A of the paper culture apparatus obtained in the step 3); and
   5) immersing the surface B of the apparatus obtained in the step 4) into a glass culture dish containing a BG-11 culture solution for culture;
   wherein the first agar aqueous solution is prepared by the following method: weighing 0.8 g to 1.5 g of agar, adding water to 100 ml, mixing uniformly, and heating to dissolve; and
   the second agar aqueous solution is prepared by the following method: weighing 0.1 g to 0.5 g of agar, adding water to 100 ml, mixing uniformly, and heating to dissolve.

2. The method according to claim 1, wherein the number of circles on the culture apparatus ranges from 6 to 96.

3. The method according to claim 1, wherein the filter paper is a piece of qualitative filter paper or quantitative filter paper.

4. The method according to claim 1, wherein the condition for culture in the step (4) is as follows: irradiating at the temperature ranges from 20° C. to 35° C. for 4 to 8 days.

* * * * *